US009700679B2

(12) United States Patent
Butler et al.

(10) Patent No.: US 9,700,679 B2
(45) Date of Patent: Jul. 11, 2017

(54) DRIVE MECHANISM FOR A DRUG DELIVERY DEVICE AND DRUG DELIVERY DEVICE

(71) Applicant: SANOFI-AVENTIS DEUTSCHLAND GMBH, Frankfurt am Main (DE)

(72) Inventors: Stephen David Butler, South Staffordshire (GB); Mark Philip Horlock, Cheshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 98 days.

(21) Appl. No.: 14/401,942

(22) PCT Filed: May 28, 2013

(86) PCT No.: PCT/EP2013/060911
§ 371 (c)(1),
(2) Date: Nov. 18, 2014

(87) PCT Pub. No.: WO2013/178599
PCT Pub. Date: Dec. 5, 2013

(65) Prior Publication Data
US 2015/0088079 A1    Mar. 26, 2015

(30) Foreign Application Priority Data

May 30, 2012    (EP) ..................... 12170066

(51) Int. Cl.
*A61M 5/315*    (2006.01)
*A61M 5/24*    (2006.01)

(52) U.S. Cl.
CPC .......... *A61M 5/31595* (2013.01); *A61M 5/24* (2013.01); *A61M 5/3155* (2013.01);
(Continued)

(58) Field of Classification Search
CPC .. A61M 5/24; A61M 5/31543; A61M 5/3155; A61M 5/31551
See application file for complete search history.

(56) References Cited

U.S. PATENT DOCUMENTS 6,277,099 B1    8/2001    Strowe et al.
8,092,420 B2    1/2012    Bendek et al.
(Continued)

FOREIGN PATENT DOCUMENTS

CN    102448521 A    5/2012
DE    WO 2010115818 A1 * 10/2010    ........ A62M 5/31525
(Continued)

OTHER PUBLICATIONS

International Search Report and Written Opinion for Int. App. No. PCT/EP2013/060911, mailed Jun. 24, 2013.
(Continued)

*Primary Examiner* — Kevin C Sirmons
*Assistant Examiner* — Deanna K Hall
(74) *Attorney, Agent, or Firm* — McDonnell Boehnen Hulbert & Berghoff LLP

(57) ABSTRACT

The drive mechanism for a drug delivery device comprises a piston rod, which is displaced in a distal direction for a delivery of a dose and in a proximal direction for a reset, and a resilient member, which acts on the piston rod during a reset and tends to restrict the movement of the piston rod in the proximal direction. The resilient member may be a biasing member provided for an automatic reset, a compression spring entering the piston rod or a torsion spring provided to generate a rotation. The drug delivery device is provided with such a drive mechanism.

18 Claims, 3 Drawing Sheets

(52) U.S. Cl.
   CPC .... *A61M 5/31501* (2013.01); *A61M 5/31543* (2013.01); *A61M 5/31551* (2013.01); *A61M 5/31585* (2013.01)

(56) References Cited

U.S. PATENT DOCUMENTS

2004/0210199 A1* 10/2004 Atterbury ......... A61M 5/31566
                                                         604/224
2012/0101452 A1    4/2012 Harms et al.

FOREIGN PATENT DOCUMENTS

| EP | 2196232       | 6/2010  |
|----|---------------|---------|
| GB | 2461732       | 1/2010  |
| WO | 2009/097934 A1 | 8/2009  |
| WO | 2010/115818 A1 | 10/2010 |
| WO | 2011/154482 A2 | 12/2011 |

OTHER PUBLICATIONS

Chinese Office Action for Chinese Patent Application No. 201380026645.6, issued Jul. 26, 2016.
Chinese Search Report for Chinese Patent Application No. 201380026645.6, dated Jul. 15, 2016.
Second Chinese Office Action for CN Application No. 201380026645.6, issued Feb. 13, 2017.
Chinese Search Report for CN Application No. 201380026645.6, dated Feb. 5, 2017.

\* cited by examiner

DRIVE MECHANISM FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2013/060911 filed May 28, 2013, which claims priority to European Patent Application No. 12170066.0 filed May 30, 2012. The entire disclosure contents of these applications are herewith incorporated by reference into the present application.

TECHNICAL FIELD

The present invention relates to a drive mechanism for a reusable drug delivery device and a reusable drug delivery device incorporating such a drive mechanism.

BACKGROUND

EP 2 196 232 A1 describes a drive mechanism for a medication delivery device comprising a housing having a proximal end and a distal end, a rotation member which is rotated in a first direction during setting of a dose and rotated in an opposite second direction during delivery of the dose, a piston rod, which is adapted to be displaced in a distal direction with respect to the housing for delivering the dose, a drive member, which follows rotational movement of the rotation member in the second direction during delivery of the dose, and a stop member, which prevents rotational movement of the drive member with respect to the housing in the first direction during setting of the dose. The rotational movement of the drive member in the second direction is converted into movement of the piston rod in the distal direction with respect to the housing. The medication delivery device is provided with the drive mechanism and with a cartridge containing the medication. An empty cartridge can be replaced with a new cartridge, so that the medication delivery device is reusable. The replacement of the cartridge requires a reset of the piston rod to an initial position at the proximal end. A priming operation is performed to bring the piston rod in contact with the piston of the new cartridge.

U.S. Pat. No. 6,277,099 describes a medication delivery device comprising a lead screw for medication delivery. A priming operation required after a change of the cartridge is supported by the lead screw being forward biased by a lead screw spring.

SUMMARY

The invention relates to a new drive mechanism for a drug delivery device, particularly for a reusable drug delivery device, providing an effective reset operation. The invention further relates to a new drug delivery device, particularly a reusable drug delivery device, wherein the change of a drug container is facilitated.

This is achieved with a drive mechanism according to claim 1 and with a drug delivery device according to claim 11. Embodiments and variants derive from the dependent claims.

According to one aspect, a drive mechanism for a drug delivery device is presented which comprises a piston rod, which is displaced in a distal direction for a delivery of a dose and in a proximal direction for a reset, and a resilient member, which acts on the piston rod during a reset and tends to restrict the movement of the piston rod in the proximal direction. The resilient member is selected from the group consisting of a biasing member provided for an automatic reset, a compression spring entering the piston rod, and a torsion spring provided to generate a rotation.

According to an embodiment the drive mechanism further comprises a rotatable drive member, which is threadedly engaged with the piston rod and rotates during the delivery of the dose. The resilient member is a biasing member, which is loaded by the rotation of the drive member during the delivery of the dose and tends to rotate the piston rod with respect to the drive member in such a way that the piston rod is screwed into the drive member and thereby advanced in the proximal direction, until the biasing member is relaxed and the movement of the piston rod in the proximal direction is stopped.

According to a further embodiment of the drive mechanism the biasing member is a helical spring arranged coaxially with the piston rod.

According to a further embodiment the drive mechanism further comprises a housing, a lock nut releasably rotationally locked to the housing and threadedly engaged with the piston rod, and a cartridge holder, which can be attached or removed, the lock nut being rotationally locked with the housing when the cartridge holder is attached and not being rotationally locked with the housing when the cartridge holder is removed. The biasing member is latched to the lock nut and to the drive member so that the biasing member is loaded when the drive member rotates relative to the housing during the delivery of the dose. The biasing member relaxes when the rotational locking of the lock nut is removed, resulting in a rotation of the lock nut and a corresponding rotation of the piston rod with respect to the drive member.

According to a further embodiment the drive mechanism further comprises a centralizing rod. The resilient member is a compression spring formed by a helical spring with the centralizing rod arranged coaxially with the helical spring.

According to a further embodiment of the drive mechanism the piston rod has a hollow cylindrical shape opening in the proximal direction, and the compression spring and the centralizing rod enter the piston rod and extend beyond the piston rod in the proximal direction.

According to a further embodiment the drive mechanism further comprises a rotatable drive member, which is threadedly engaged with the piston rod and rotates during the delivery of the dose, and a dose member, which is coupled, particularly threadedly engaged with the drive member, either permanently or in a releasable manner, for example, and is provided for setting a dose. The resilient member is a torsion spring that engages the dose member and tends to rotate the dose member in such a way that a rotation of the drive member is generated which advances the piston rod in the distal direction.

According to a further embodiment the drive mechanism further comprises a housing, a lock nut releasably rotationally locked to the housing and threadedly engaged with the piston rod, and a cartridge holder, which can be attached or removed. The lock nut is rotationally locked with the housing when the cartridge holder is attached and not rotationally locked with the housing when the cartridge holder is removed. The piston rod is displaced during the delivery of the drug in the distal direction in a helical movement with respect to the housing, and the movement of the piston rod is guided by the threaded engagement of the piston rod with the rotationally locked lock nut.

According to a further embodiment of the drive mechanism the threaded engagement of the lock nut with the piston rod is effected by a screw thread and the threaded engagement of the drive member with the piston rod is effected by a further screw thread. The ratio of the distances which are travelled by the drive member and the piston rod during the delivery of the drug is determined by the pitches of the screw thread and the further screw thread.

According to a further embodiment of the drive mechanism the torsion spring is loaded by rotating the dose member to set a dose.

Another aspect relates to a drug delivery device comprising a drive mechanism as described above.

According to an embodiment the drug delivery device comprises a removable cartridge holder that is provided for a cartridge to be inserted. The resilient member acts on the piston rod during a reset and tends to restrict the movement of the piston rod in the proximal direction.

According to a further embodiment the drug delivery device further comprises a drive member for a delivery of a dose and a dose member for setting a dose. The drive member and the dose member are threadedly engaged. The resilient member is a torsion spring that engages the dose member and tends to rotate the dose member in such a way that a rotation of the drive member is generated which advances the piston rod in the distal direction.

According to a further embodiment the drug delivery device is a pen-type device.

According to a further embodiment the drug delivery device is provided to deliver fixed doses.

Features which are described herein above and below in connection with the drive mechanism may also be applied for the corresponding drug delivery device and vice versa.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-sn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The following is a further explanation of the invention and its advantages by a detailed description of exemplary embodiments in conjunction with the accompanying drawings.

DETAILED DESCRIPTION

Figure 1:
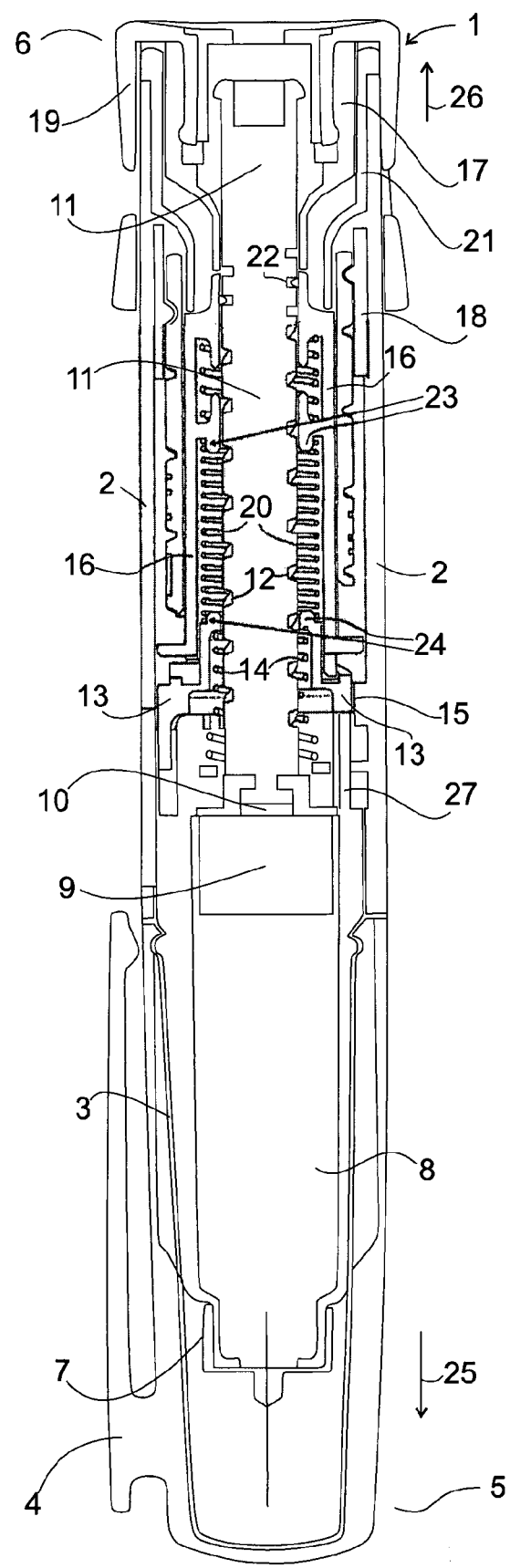
FIG. 1 shows a cross-section of an example of a pen-type drug delivery device.

FIG. 1 shows a cross section of a drug delivery device 1 with a drive mechanism, which is arranged in a housing 2 comprising a removable and attachable cartridge holder 3, in which a cartridge 8 containing a drug can be inserted. The housing may be any body or assembly of exterior parts that enable the handling of the drug delivery device or its mechanism. It may be designed to house, fix, protect, guide, and/or engage with any of the components of a drive mechanism, preferably by limiting the exposure to contaminants, such as liquid, dust, dirt etc. In general, the housing may be unitary or a multipart component of tubular or non-tubular shape. The drug or medication retained in the cartridge 8 is preferably a liquid drug and may particularly be any of the abovementioned drugs. The cartridge 8 may contain a plurality of doses of the drug. The device 1 may be configured to dispense fixed or variable doses of the drug.

The device 1 has a distal end 5 and a proximal end 6. The term "distal end" designates that end of the drug delivery device or a component thereof which is or is to be arranged closest to a dispensing end of the drug delivery device. The term "proximal end" designates that end of the device or a component thereof which is or is to be arranged furthest away from the dispensing end of the device. The term "distal direction" 25 means the direction from the proximal end 6 towards the distal end 5. The term "proximal direction" 26 means the direction from the distal end 5 towards the proximal end 6. The device 1 may be an injection device, particularly a pen-type injector. The device 1 may be a needle-based or a needle free device. A cap 4 may be provided to cover the distal end 5, where a needle assembly 7 may be provided to deliver a drug from the cartridge 8.

The drug is expelled from the cartridge 8 by means of a piston 9, which is driven by a piston rod 11 of the drive mechanism. The piston rod 11 is a component that is adapted to transfer an axial movement to the piston 9 in the distal direction 25 and may be a simple rod, a leadscrew, a rack-and-pinion system, a worm gear system, or the like. It may be made of any suitable material and may be of unitary or multipart construction. The piston rod 11 preferably engages the piston 9 by means of a bearing 10, which is provided to enable a rotation between the piston 9 and the piston rod 11.

The piston rod 11 may have the shape of a leadscrew and may be provided with a screw thread 12, which enables an engagement with a lock nut 13, which guides a helical movement of the piston rod 11 with respect to the housing 1. The lock nut 13 is releasably rotationally locked with the housing 1, so that a rotation of the piston rod 11 relative to the housing 1 is restricted to the helical movement guided by the screw thread 12. When the cartridge holder 3 is removed from the main part of the housing 1, the rotational locking of the lock nut 13 is also removed, and the piston rod 11 is free to rotate with respect to the housing 1. The rotational locking of the lock nut 13 may be removed by an axial shift of the lock nut 13 in the distal direction 25, for example, and the shift may be effected by a resilient means, which may be a release spring 14, for example. When the cartridge holder 3 is attached, the lock nut 13 is shifted in the proximal direction 26 until it engages with a locking means 15 of the housing 1 and is rotationally locked by the locking means 15.

The drive mechanism further comprises a rotatable drive member 16 which is threadedly engaged with the piston rod 11. The drive member 16 rotates relative to the housing 1 and hence relative to the lock nut 13 during a delivery operation. The engagement of the drive member 16 with the piston rod 11 may be effected by a further screw thread 22. A dose member 17 may be provided for a dosing operation, which may be taken account of by a counter 18. A button 19, which can be pulled or screwed in the proximal direction 26 and pushed in the distal direction 25, may be provided at the proximal end 6 as a means to operate the drive mechanism. By pushing the button 19, a force is transferred to the piston rod 11 via the drive mechanism to drive the piston 9 with respect to the cartridge 8 in the distal direction 25. The ratio of the distances which are travelled by the button 19 and the piston 9 or, correspondingly, the ratio of the distances which are travelled by the drive member 16 and the piston rod 11 is determined by the design of the drive mechanism, especially by the pitches of the screw threads 12, 22 that guide the movement of the piston rod 11. A dose of the drug may be dispensed from the cartridge in this way. The delivered dose is determined by the distance by which the piston 9 is displaced with respect to the cartridge 8 in the distal direction 25. The invention is suitable to incorporate a great variety of constructions that are suitable to drive the piston rod 11 by predetermined distances in order to expel the appropriate doses of the drug.

The drive mechanism comprises a biasing member 20, which may be a resilient member like a spring, especially a helical spring, for example. The biasing member 20 is fastened to the lock nut 13 and the drive member 16 in such a manner that the biasing member 20 is loaded by a rotation of the drive member 16, provided that the cartridge holder 3 is attached. When the cartridge holder 3 is removed from the main part of the housing 1 and the rotational locking of the lock nut 13 with respect to the housing 1 is also removed, the lock nut 13 is free to rotate relative to the drive member 16. Consequently the loaded biasing member 20 relaxes and rotates the lock nut 13 relative to the drive member 16 in such a manner that the piston rod 11 is screwed back into the drive member 16 in the proximal direction 26. The drive mechanism may be designed in such a manner that the counter 18 is also automatically reset when the piston rod 11 is reset. The counter 18 may comprise a rotatable sleeve, for instance, which may be rotated simultaneously with the piston rod 11 when the biasing member 20 relaxes.

The biasing member 20 is further provided to generate a force that drives the piston rod 11 in the distal direction 25 if the piston rod 11 moves in the proximal direction 26 beyond a position that is appropriate as a start position. The biasing member 20 thus guarantees that after a reset the piston rod 11 occupies exactly the position that is appropriate for the delivery of the first dose from a new cartridge. It is therefore not necessary to perform a dedicated priming step. When the cartridge holder 3 is attached the piston rod 11 is automatically brought into contact with the piston 9 or the bearing 10, respectively. If the automatic reset function is not desired, the biasing member 20 may be latched directly to the housing 2 or any other element that is rotationally locked to the housing 2, because in this case the only relevant movement is the relative rotation between the housing 2 and the drive member 16 which loads the biasing member 20. When the piston rod 11 is reset in the proximal direction 26 beyond the start position, the biasing member 20 is loaded in the opposite direction and tends to rotate the drive member 16 in such a way that it causes the piston rod 11 to advance in the distal direction 25 to the accurately primed position.

Figure 2:
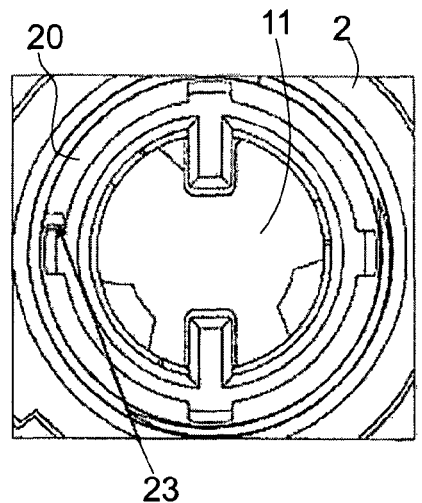
FIG. 2 shows a further cross-section as indicated in FIG. 1.

FIG. 2 shows the cross-section that is indicated in FIG. 1. FIG. 2 shows how the biasing member 20 may be latched to the drive member 16 by means of a protrusion 23 or indentation on the drive member 16. In the embodiment according to FIG. 2 the biasing member 20 is a helical spring surrounding the piston rod 11. The protrusion 23 or indentation is formed to function as a stop at one end of the biasing member 20 and prevents this end of the biasing member 20 from rotating in the direction that is opposite to the direction in which the biasing member 20 is loaded. Thus the protrusion 23 or indentation prevents the biasing member 20 from relaxing as long as the lock nut 13 is rotationally locked to the housing 1.

Figure 3:
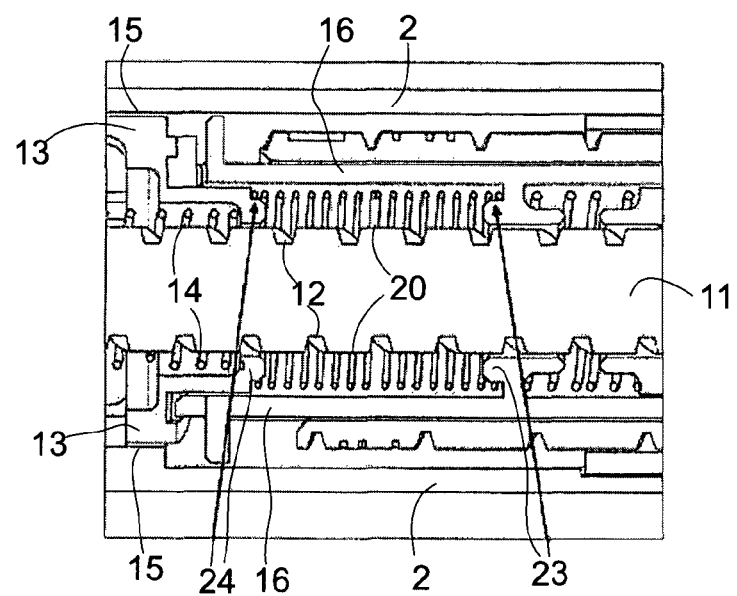
FIG. 3 shows a detail of the cross-section of FIG. 1.

FIG. 3 shows a detail of the cross-section according to FIG. 1. FIG. 3 shows how opposite ends of the biasing member 20 are latched to the lock nut 13 and to the drive member 16 in such a way that a relative rotation of the drive member 16 with respect to the lock nut 13 effects a torsion of the biasing member 20, thereby loading the biasing member 20. The lock nut 13 may be provided with a further protrusion 24 or indentation, which is formed to function as a stop at one end of the biasing member 20 and, in conjunction with the latch effected by the protrusion 23 or indentation on the drive member 16, prevents the biasing member 20 from relaxing as long as the lock nut 13 is rotationally locked to the housing 1. When the lock nut 13 is rotationally free, the biasing member 20 generates a rotation of the lock nut 13 with respect to the drive member 16, and due to the engagement of the piston rod 11 with the lock nut 13 and with the drive member 16, the piston rod 11 is automatically screwed back into the drive member 16 in the proximal direction 26. In this way a removal of the cartridge holder 3 causes an automatic reset of the piston rod 11 to a start position which fits the initial position of the piston 9 within the full new cartridge 8 when it is inserted and the cartridge holder 3 is attached to the housing 1.

Although a helical spring is particularly suitable, other resilient elements may be used as the biasing member 20. The biasing member 20 may be a separate element or an integral part of the lock nut 13 or the drive member 16.

Figure 4:
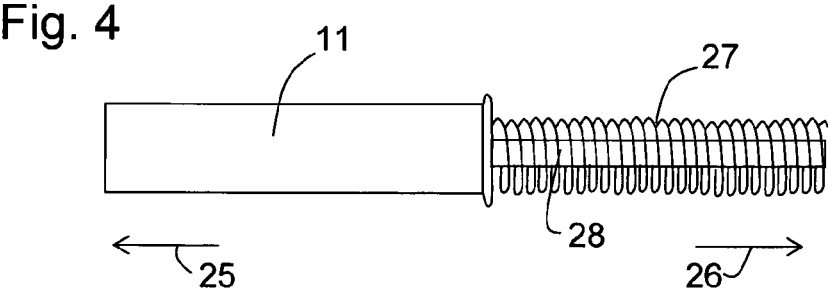
FIG. 4 shows an arrangement of the piston rod and a compression spring.
Figure 5:
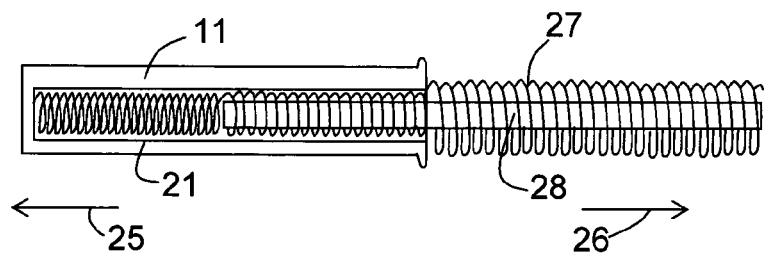
FIG. 5 shows a cross-section of the arrangement according to FIG. 4.

FIGS. 4 and 5 show an arrangement of the piston rod 11 for a further embodiment having a compression spring 27, which may be guided by a centralizing rod 28. The piston rod 11 has a hollow cylindrical shape, and the compression spring 27 and the centralizing rod 28 enter the interior 21 of the piston rod 11. The compression spring 27 is adapted to drive the piston rod 11 in the distal direction 25 in such a manner that the piston rod 11 advances in the distal direction 25 to the accurately primed position. FIG. 5 shows a cross-section of the piston rod 11 with the compression spring 27 acting on the bottom of the interior 21 of the piston rod 11 and exerting a force in the distal direction 25 and the centralizing rod 28 reaching about half way into the interior 21 of the piston rod 11. The centralizing rod 28 is primarily used outside the piston rod 11 to keep the compression spring 27 in the axial direction, while the compression spring 27 is axially guided within the piston rod 11 by the inner walls of the interior 21.

Figure 6:
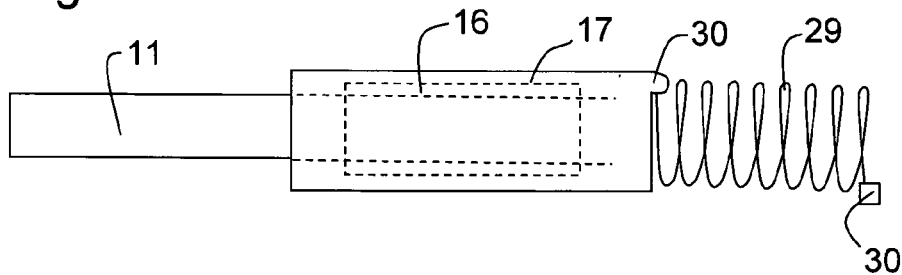
FIG. 6 shows an arrangement of the piston rod and a torsion spring.
Figure 7:
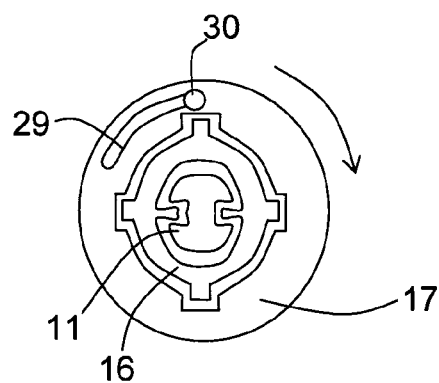
FIG. 7 shows a cross-section of the arrangement according to FIG. 6.

FIGS. 6 and 7 show an arrangement of the piston rod 11 for a further embodiment having a drive member 16, a dose member 17, and a torsion spring 29. The dose member 17 is coupled with the drive member 16, particularly threadedly engaged with the drive member 16, either permanently or in a releasable manner, for example. The torsion spring 29 is latched to the dose member 17 and to a part of the housing 2 or an element that is rotationally locked with the housing 2, which may be effected by means of lugs 30, for instance. FIG. 7 shows the arrangement in the axial direction. The piston rod 11, the drive member 16, and the dose member 17 are rotationally, but not axially locked. The torsion spring 29, of which one end is shown in FIG. 7, is latched to the lug 30 of the dose member 17 and is loaded to generate a rotation of the dose member 17 according to the curved arrow. This rotation is transferred to the drive member 16, which drives the piston rod 11 in the distal direction so that the piston rod 11 advances in the distal direction 25 to the accurately primed position.

The drive mechanism using a resilient element driving the piston rod in the distal direction has the advantages that after a change of the cartridge the piston rod will at once be in contact with the piston or the bearing of the piston and that there is no need for a dedicated priming step to be performed by the user.

The described drive mechanism is suitable for a drug delivery device, especially a reusable drug delivery device. The drug delivery device may be a pen-type device, especially a pen-type injector, for example. The drive mechanism is particularly suitable for a device that is designed for the delivery of fixed doses.

The invention claimed is:
1. A drive mechanism for a drug delivery device, comprising:
   a housing;
   a piston rod, which is displaced in a distal direction for a delivery of a dose and in a proximal direction for a reset;
   a drive member engaged with the piston rod and configured to drive the piston rod in the distal direction during dose delivery, wherein the drive member is rotatable relative to the housing during the dose delivery; and
   a resilient member which is loaded by a rotation of the drive member with respect to the housing and acts on the piston rod during a reset and tends to restrict the movement of the piston rod in the proximal direction,
wherein the resilient member is selected from the group consisting of a biasing member provided for an automatic reset and a torsion spring provided to generate a rotation.

2. The drive mechanism of claim 1,
wherein the drive member is threadedly engaged with the piston rod and rotates during the delivery of the dose, and
wherein the resilient member is a biasing member, which is loaded by the rotation of the drive member during the delivery of the dose and tends to rotate the piston rod with respect to the drive member in such a way that the piston rod is screwed into the drive member and thereby advanced in the proximal direction, until the biasing member is relaxed and the movement of the piston rod in the proximal direction is stopped.

3. The drive mechanism of claim 2, wherein the biasing member is a helical spring arranged coaxially with the piston rod.

4. The drive mechanism of claim 1, further comprising:
a lock nut releasably rotationally locked to the housing and threadedly engaged with the piston rod, and
a cartridge holder, which can be attached or removed, the lock nut being rotationally locked with the housing when the cartridge holder is attached and not being rotationally locked with the housing when the cartridge holder is removed, wherein
the biasing member is latched to the lock nut and to the drive member so that the biasing member is loaded when the drive member rotates relative to the housing during the delivery of the dose, and
the biasing member relaxes when the rotational locking of the lock nut is removed, resulting in a rotation of the lock nut and a corresponding rotation of the piston rod with respect to the drive member.

5. The drive mechanism of claim 1, further comprising:
a centralizing rod coaxial with the piston rod, wherein the centralized rod extends proximally from the piston rod; and
a compression spring formed by a helical spring with the centralizing rod arranged coaxially within the helical spring.

6. The drive mechanism of claim 5, wherein
the piston rod includes a bore extending from a proximal end of the piston rod, and
wherein the compression spring and the centralizing rod enter the bore of the piston rod at a first end and extend beyond the piston rod in the proximal direction at a second end.

7. The drive mechanism of claim 1, wherein the drive member is threadedly engaged with the piston rod and rotates during the delivery of the dose, and
a dose member, which is coupled with the drive member and is provided for setting a dose,
wherein the resilient member is a torsion spring that engages the dose member and tends to rotate the dose member in such a way that a rotation of the drive member is generated which advances the piston rod in the distal direction.

8. The drive mechanism of claim 7, further comprising:
a lock nut releasably rotationally locked to the housing and threadedly engaged with the piston rod, and
a cartridge holder, which can be attached or removed,
the lock nut being rotationally locked with the housing when the cartridge holder is attached and not being rotationally locked with the housing when the cartridge holder is removed,
wherein the piston rod is displaced during the delivery of the drug in the distal direction in a helical movement with respect to the housing, the movement of the piston rod being guided by the threaded engagement of the piston rod with the rotationally locked lock nut.

9. The drive mechanism of claim 8, wherein
the threaded engagement of the lock nut with the piston rod is effected by a screw thread and the threaded engagement of the drive member with the piston rod is effected by a further screw thread, and
the ratio of the distances which are travelled by the drive member and the piston rod during the delivery of the drug is determined by the pitches of the screw thread and the further screw thread.

10. The drive mechanism of claim 7, wherein
the torsion spring is loaded by rotating the dose member to set a dose.

11. The drive mechanism of claim 1, wherein the mechanism comprises a housing and a drive member, which is engaged with the piston rod and rotatable with respect to the housing.

12. The drive mechanism of claim 1, wherein the resilient member is provided to drive the piston rod in the distal direction to a start or primed position.

13. A drug delivery device comprising a drive mechanism according to claim 1.

14. The drug delivery device of claim 13, wherein
the device comprises a removable cartridge holder that is provided for a cartridge to be inserted, and
the resilient member acts on the piston rod during a reset and tends to restrict the movement of the piston rod in the proximal direction.

15. The drug delivery device of claim 14, a dose member for setting a dose, the drive member and the dose member being threadedly engaged, the resilient member being a torsion spring that engages the dose member and tends to rotate the dose member in such a way that a rotation of the drive member is generated which advances the piston rod in the distal direction.

16. The drug delivery device of claim 13, wherein the device is a pen-type device.

17. The drug delivery device of claim 13, wherein the device is provided to deliver fixed doses.

18. The drive mechanism of claim 1, wherein the resilient member is the biasing member which is provided for the automatic reset, wherein the automatic reset is automatically initiated responsive to removal of a cartridge holder from the housing.

* * * * *